(12) United States Patent
Rodriguez Baixauli et al.

(10) Patent No.: US 8,785,725 B2
(45) Date of Patent: Jul. 22, 2014

(54) METHOD FOR GENERATING RESISTANCE AGAINST CITRUS DISEASES CAUSED BY INSECTS, FUNGI, OOMYCETES, BACTERIA OR NEMATODES

(75) Inventors: Ana Rodriguez Baixauli, Moncada (ES); Magdalena Cervera Ocaña, Moncada (ES); Takehiko Shimada, Moncada (ES); Lluis Palou Vall, Moncada (ES); Lorenzo Zacarias Garcia, Moncada (ES); Maria Milagros Lopez Gonzalez, Moncada (ES); Leandro Peña Garcia, Moncada (ES); Pedro Castañera Domínguez, Moncada (ES); Victoria San Andres Aura, Moncada (ES); Maria Jesús Rodrigo Esteve, Moncada (ES); Ana Redondo Puntonet, Moncada (ES)

(73) Assignee: Institute Valenciano de Investigaciones Agrarias (ES)

(*) Notice: Subject to any disclaimer, the term of this patent is extended or adjusted under 35 U.S.C. 154(b) by 340 days.

(21) Appl. No.: 12/945,972

(22) Filed: Nov. 15, 2010

(65) Prior Publication Data
US 2011/0119788 A1    May 19, 2011

(30) Foreign Application Priority Data
Nov. 18, 2009   (ES) .................................. 200902183

(51) Int. Cl.
*C12N 15/82*   (2006.01)
*C12N 9/88*    (2006.01)

(52) U.S. Cl.
CPC ........ *C12N 15/8286* (2013.01); *C12N 15/8282* (2013.01); *C12N 15/8285* (2013.01); *C12N 9/88* (2013.01); *C12N 15/8247* (2013.01); *C12N 15/8281* (2013.01)
USPC ............................ 800/279; 800/285; 800/286

(58) Field of Classification Search
None
See application file for complete search history.

(56) References Cited

PUBLICATIONS

De Moraes et al, 1998, Nature, 393:570-573.*
Carroll et al, 2006, J. Chem. Ecol. 32:1911-1924.*
Endo et al, 2009, J. Japan. Soc. Hort. Sci., 78:74-83.*
Chen et al, 2003, Plant J., 36:731-740.*
Nakatsuka et al, 2007, Plant Biotechnol. Rep., 1:251-257.*
Ghorbel et al, 2000, Tree Phys., 20:1183-1189.*
A. Aharoni et al., "Terpenoid Metabolism in Wild-Type and Transgenic *Arabidopsis* Plants", The Plant Cell, vol. 15, pp. 2866-2884 (2003).
G. Arimura et al., "Herbivory-induced volatiles elicit defence genes in lima bean leaves", Nature, vol. 406, pp. 512-515 (2000).
G. Bisignano et al., "The biological activity of citrus oils", Medicinal and Aromatic Plants-Industrial Profiles, Chapter 28, pp. 602-630 (2002).
C.M. DeMoraes et al., "Caterpillar-induced nocturnal plant volatiles repel conspecific females", Nature, vol. 410, pp. 577-580 (2001).
J. Degenhardt et al., "Restoring a maize root signal that attracts insect-killing nematodes to control a major pest", PNAS, vol. 106, No. 32, pp. 13213-13218 (2009).
T. Endo et al., "Development of a *CiFT* Co-expression System for Functional Analysis of Genes in Citrus Flowers and Fruit", J. Japan. Soc. Hort. Sci. 78 (1), pp. 74-83 (2009).
J. Gershenzon et al., "The function of terpene natural products in the natural world", Natural Chemical Biology, vol. 3, No. 7, pp. 408-414 (2007).
S. Goff et al., "Plant Volatile Compounds: Sensory Cues for Health and Nutritional Value?", Science, vol. 311, pp. 815-819 (2006).
I.F. Kappers et al., "Genetic Engineering of Terpenoid Metabolism Attracts Bodyguards to *Arabidopsis*", Science, vol. 309, pp. 2070-2072 (2005).
D. Kessler et al., "Field Experiments with Transformed Plants Reveal the Sense of Floral Scents", Science, vol. 321, pp. 1200-1202 (2008).
J. Lücker et al., "Monoterpene biosynthesis in lemon (*Citrus* limon) cDNA isolation and functional analysis of four monoterpene synthases", Eur. J. Biochem, vol. 269, pp. 3160-3171 (2002).
J. Lücker et al., "Increased and Altered Fragrance of Tobacco Plants after Metabolic Engineering Using Three Monoterpene Synthases from Lemon", Plant Physiology, vol. 134, pp. 510-519 (2004).
L. Peña et al., "Transgenic Tropical and Subtropical Fruits and Nuts", Copendium of Transgenic Crop Plants, Chapter 1, vol. 5, pp. 1-61 (2008).
M.J. Rodrigo et al., Biochemical and Molecular Analysis of Carotenoid Biosynthesis in Flavedo of Orange (*Citrus* sinesis L.) during Fruit Development and Maturation, J. Agric. Food. Chem., vol. 52, pp. 6724-6731 (2004).
C. Schnee et al., "The products of a single maize sesquiterpene synthase form a volatile defense signal that attracts natural enemies of maize herbivores", PNAS, vol. 103, No. 4, pp. 1129-1134 (2006).
T. Shimada et al., "Molecular cloning and functional characterization of four monoterpene synthase genes from *Citrus unshiu* Marc", Plant Science, vol. 166, pp. 49-58 (2004).
T. Shimada et al., "Isolation and characterization of a new *d*-limonene synthase gene with a different expression pattern in *Citrus unshiu* Marc", Scientia Horticulturae, vol. 105, pp. 507-512 (2005).

(Continued)

*Primary Examiner* — Ashwin Mehta
*Assistant Examiner* — Jason Deveau Rosen
(74) *Attorney, Agent, or Firm* — Ostrolenk Faber LLP (57) ABSTRACT

The invention consists in modifying the levels of accumulation and emission of monoterpenes and sesquiterpenes in citrus as a mechanism to achieve systemic resistance against pathogens or repellency against pests. The alteration of the content of d-limonene and other terpenes is achieved by genetic transformation via the introduction of a gene that encodes an enzyme with d-limonene synthase activity, from a citrus fruit or plant or from another living organism, in anti-sense or RNAi (RNA interference) configuration. Genetic modification is achieved either by *Agrobacterium tumefaciens* or any other method of genetic transformation of plants from protoplasts or explants. The construction is incorporated in citrus genotypes or related genera of the family Rutaceae in order to reduce the levels of accumulation and emission of the monoterpene and precursor compounds and/or derivatives, either of leaves or flowers and/or fruit.

20 Claims, 6 Drawing Sheets

(56) References Cited

PUBLICATIONS

S. Trapp et al., "Defensive Resin Biosynthesis in Conifers", Annu. Rev. Plant Physiol and Plant Mol. Biol., vol. 52, pp. 689-724 (2001).

S. Wu et al., "Redirection of cytosolic or plastidic isoprenoid precursors elevates terpene production in plants", Nature Biotechnology, vol. 24, No. 11, pp. 1441-1447 (2006).

* cited by examiner

```
   1 ATGTCTTCTT GCATTAATCC CTCAACCTTG GCTACCTCTG TAAATGGTTT
  51 CAAATGTCTT CCTCTTGCAA CAAATAGAGC AGCCATCAGA ATCATGGCAA
 101 AAAATAAGCC AGTCCAATGC CTTGTCAGCA CCAAATATGA TAATTTGACA
 151 GTTGATAGGA GATCAGCAAA CTACCAACCT TCAATTTGGG ACCATGATTT
 201 TTTGCAGTCA CTGAATAGCA ACTATACGGA TGAAACATAC AAAAGACGAG
 251 CAGAAGAGCT GAAGGGAAAA GTGAAGACAG CGATTAAGGA TGTAACCGAG
 301 CCTCTGGATC AGTTGGAGCT GATTGATAAT TTGCAAAGAC TTGGATTGGC
 351 TTATCATTTT GAGCCTGAGA TTCGGAACAT ATTGCGTAAT ATCCACAACC
 401 ATAATAAAGA TTATAATTGG AGAAAAGAAA ATCTGTATGC AACCTCCCTT
 451 GAATTCAGAC TACTTAGACA ACATGGCTAT CCTGTTTCTC AAGAGGTTTT
 501 CAGTGGTTTT AAAGACGACA AGGTAGGCTT CATTTGTGAT GATTTCAAGG
 551 GAATACTGAG CTTGCATGAA GCCTCGTATT ACAGCTTAGA AGGAGAAAGC
 601 ATCATGGAGG AGGCCTGGCA ATTCACCAGT AAGCATCTTA AGAAATGAT
 651 GATCATCAGC AACAGCAAGG AAGAGGATGT ATTTGTAGCA GAACAAGCGA
 701 AGCGGGCGCT GGAGCTCCCT CTGCATTGGA AAGTGCCTAT GTTAGAGGCA
 751 AGGTGGTTCA TACACGTTTA TGAGAAAAGA GAGGACAAGA ACCACCTTTT
 801 ACTTGAGCTC GCTAAGTTGG AGTTTAACAC TTTGCAGGCA ATTTACCAGG
 851 AAGAACTTAA AGACATTTCA GGGTGGTGGA AGGATACAGC TCTTGGAGAG
 901 AAATTGAGCT TTGCGAGGAA CAGGTTGGTA GCGTCCTTCT TATGGAGCAT
 951 GGGGATCGCG TTTGAGCCTC AATTCGCCTA CTGCAGGAGA GTGCTCACAA
1001 TCTCGATAGC CCTAATTACA GTGATTGATG ACATTTATGA TGTCTATGGA
1051 ACATTGGATG AACTTGAGAT ATTCACTGAT GCTGTTGAGA GGTGGGACAT
1101 CAATTATGGT TTGAAGCACC TTCCGGGCTA TATGAAAATG TGTTTTCTTG
1151 CCCTTTACAA CTTTGTTAAT GAATTTGCTT ATTACGTTCT CAAACAACAG
1201 GATTTTGATA TGCTTCTGAG CATAAAACAT GCATGGCTTG GCTTAATACA
1251 AGCCTACTTG GTGGAGGCGA ATGGTACCA TAGCAAGTAC ACACCGAAAC
1301 TGGAAGAATA CTTGGAAAAT GGATTGGTAT CAATAACGGG CCCTTTAATT
1351 ATAACGATTT CATATCTTTC TGGTACAAAT CCAATCATTA GAAGGAACT
1401 GGAATTTCTA GAAAGTAATC CAGATATAGT TCACTGGTCA TCCAAGATTT
1451 TCCGTCTGCA AGATGATTTG GAACTTCAT CGGACGAGAT ACAGAGAGGG
1501 GATGTTCCGA AATCAATCCA GTGTTACATG CATGAAACTG GTGCCTCGGA
1551 GGAAGTTGCT CGTGAACACA TCAAGGATAT GATGAGACAG ATGTGGAAGA
1601 AGGTGAATGC ATACACAGCC GATAAAGACT CTCCCTTGAC TCGAACAACT
1651 GCTGAGTTCC TCTTGAATCT TGTGCGAATG TCCCATTTTA TGTATCTACA
1701 TGGAGATGGG CATGGTGTTC AAAACCAAGA GACTATCGAT GTCGGCTTTA
1751 CATTGCTTTT TCAGCCCATT CCCTTGGAGG ACAAAGACAT GGCTTTCACA
1801 GCATCTCCTG GCACCAAAGG CTGA     SEQ ID NO: 001
```

Fig. 1

```
MSSCNSTATSVNGKCATNRAARMAKNKVCVSTKYDNTVDRRSANYS
WDHDSNSNYTDTYKRRAKGKVKTAKDVTDDNRGAYHRNRNHNHNKD
YNWRKNYATSRRHGYVSVSGKDDKVGCDDKGSHASYYSGSMAWTSK
HKMMSNSKDVVAAKRAHWKVMARWHVYKRDKNHAKNTAYKDSGWWK
DTAGKSARNRVASWSMGAAYCRRVTSATVDDYDVYGTDTDAVRWDN
YGKHGYMKMCAYNVNAYYVKDDMSKHAWGAYVAKWYHSKYTKYNGV
STGTSYSGTNKKSNDVHWSSKRDDGTSSDRGDVKSCYMHTGASVAR
HKDMMRMWKKVNAYTADKDSTRTTANVRMSHMYHGDGHGVNTDVGT
DKDMATASGTKG
```

SEQ ID NO: 002

| Primer name | Sequence 5' – 3' |
|---|---|
| LAS-F | GAGAGGATCCATGTCTTCTTGCATTA |
| LS1-R | GAGAGGATCCTCAGCCTTTGGTGCC |
| P35S-F | ATCTCCACTGACGTAAGGGATGACG |

Figure 5

| Step | Number of cycles | Time | Temperature |
|---|---|---|---|
| Denaturing | 1 | 5 minutes | 95 °C |
| Denaturing | 35 | 30 seconds | 95 °C |
| Annealing | | 30 seconds | 58 °C |
| Elongation | | 90 seconds | 72 °C |
| Elongation | 1 | 10 minutes | 72 °C |

Figure 6

METHOD FOR GENERATING RESISTANCE AGAINST CITRUS DISEASES CAUSED BY INSECTS, FUNGI, OOMYCETES, BACTERIA OR NEMATODES

FIELD OF THE INVENTION

The present invention relates to a method for generating resistance to citrus diseases caused by insects, fungi, bacteria, oomycetes or nematodes, useful in the fields of plant pathology, entomology, fungal infections, bacterial infections, post-harvest technology, rots, plant pathogens, food processing, organoleptic attributes, improved aroma, improved flavor.

BACKGROUND OF THE INVENTION

Plants produce a wide diversity of secondary metabolites, many of which are volatile compounds emitted by leaves, flowers, roots and fruits, with different functions among which it has been found they act as signaling molecules in the interactions between plants or among distal areas from the same plant, as defense against pests and pathogens, as attractants for predators of herbivorous insects on leaves and roots, as attractants for insect pollinators in flowers, or as attractants for seed dispersal in fruits (Gershenzon and Dudareva, 2007). In addition, volatile compounds emitted by flowers are significant contributors to plant reproductive success and survival in natural ecosystems (Kessler et al., 2008). Finally, the aroma of plants and, more specifically, of their fruits, have significantly contributed to the selection of the best genotypes and their use by humans for nutritional, medicinal and industrial purposes (Goff and Klee, 2006).

In recent times, significant progress in understanding the biosynthetic pathways, in cloning important regulatory genes, in the purification of the enzymes and in the discovery of the regulatory mechanisms that lead to the formation of these volatile compounds and their emission by the different tissues or organs from plants have been achieved. Consequently, it has been proposed to use the knowledge obtained to improve plants through genetic engineering mainly with agronomic and nutritional purposes.

Citrus is the most economically important fruit tree crop in the world, with a production that exceeded 105 million tons in 2008 in an area of over 7.6 million hectares (FAO, 2009). They are grown in more than 130 countries in tropical and subtropical areas (up to 40 degrees latitude on either side of equator) where there are favorable soil and climatic conditions. The largest producers are Brazil, USA, China, Spain and Mexico, representing about 55% of world citriculture.

Citrus fruits are affected by important pests and diseases caused by nematodes, fungi, oomycetes, bacteria, spiroplasmas, phytoplasmas, viruses, viroids and diseases of unknown etiology. Some of these diseases affect most of the citrus cultivation areas, such as those caused by the oomycete *Phytophthora* sp. or by the *Citrus Tristeza Virus* (CTV), which prevent the use of certain excellent rootstocks and additionally restrict production and fruit quality in some countries. Others such as citrus canker, caused by *Xanthomonas citri* subsp. *citri*, that affects most important varieties, is widely expanded and now constitutes a serious threat to citrus in Florida and most South American countries. Other diseases are located in specific geographic areas, such as those produced by the bacterium *Xylella fastidiosa* in Sao Paulo (Brazil). Finally, there are diseases that have been locally important and in recent times have spread to other citrus-growing areas, such as Huanglongbing, caused by the bacterium *Candidatus Liberibacter* spp., affecting all varieties. This bacterium has prevented the development of a citrus industry in Southeast Asian countries and is currently destroying millions of trees in Florida and Brazil. In the case of the three above-mentioned bacteria, there are no effective means of control. There are also very important diseases affecting the post-harvesting of citrus fruits, such as those produced by fungi of the genus *Penicillium*.

Regarding pests, there are some that directly affect the green parts of the tree and/or the fruit, as the Mediterranean fruit fly (*Ceratitis capitata*) and the California red scale (*Aonidiella aurantii*), and those that are vectors of diseases such as the psyllid *Diaphorina citri*, transmitting the bacteria *Candidatus Liberibacter* spp., or the aphid *Toxoptera citricidus*, very efficient vector of CTV. Although aggressive chemicals are currently being used to control citrus pests, they do not suppose a lasting, economically and/or environmentally sustainable solution in a medium term.

Given these serious threats to the citrus industry worldwide, it is a priority to search for alternative solutions, such as those based on genetic improvement. Despite efforts in classical breeding programs over more than a century, the current citrus industry is based on a small group of high-quality varieties that are grafted on a not too wide range of rootstocks. The great majority of these genotypes have been obtained randomly, i.e. they have been got from selection of spontaneous mutations detected in the field by farmers or from chance seedlings generated by germination in a fortuitous way. In addition, breeding programs are severely limited by the complex reproductive biology of citrus. In this context, genetic modification through transgenesis offers huge potential for improvement because it allows introducing unique traits in elite genotypes without altering their genetic background. Although social controversy exists about the use of this technology for plant breeding, we believe that the use of transgenes from the own citrus genome that one wish to modify would overcome the reluctance of certain sectors and especially if this strategy proved an advantage in environmental terms over the traditional ways used to control pests and pathogens.

In the last decade, a series of fundamental works on the role of plant volatiles as repellents of pests and attractants of predators of herbivores has been published (Aharoni et al., 2003, Arimura et al., 2000, De Moraes et al., 2001). This led to think that it was possible to modulate plant volatile emission through metabolic engineering for improving the response of plant defense against pests. Thus, overexpression of the gene precursor of a linalool/nerolidol synthase from strawberry in transgenic *Arabidopsis* led to accumulation of high levels of linalool and consequently to the induction of repellency against aphids (Aharoni et al., 2003). Overexpression of this transgene in *Arabidopsis*, but this time directed to mitochondria, led to the accumulation of nerolidol and a derived homoterpene, (E)-DMNT, which made plants attractive to insect carnivore predators, natural enemies of pest mites (Kappers et al., 2005). Along these lines, overexpression of the gene precursor of a sesquiterpene synthase, TPS10, in transgenic *Arabidopsis* plants made them appealing to parasitic bees of insect pests due to the emission of high levels of sesquiterpenes which are normally released when larvae of these bees chew the leaves (Schnee et al., 2006). More recently, overexpression of the gene precursor of a trans-caryophyllene synthase from oregano in transgenic corn made the plant roots attractants of nematodes that protect them from the attack of beetles pest (Degenhardt et al., 2009). Transgenic overexpression of a precursor gene of a pachulol synthase in tobacco together with a farnesyl diphosphate synthase, precursor of sesquiterpenes, led to a high accumulation of pachulol and 13 others sesquiterpenes which made plants highly resistant to larvae of insect pests (Wu et al., 2006).

The role of different terpenoid compounds to confer resistance to pathogens is well documented, particularly in forestry, but the overexpression of precursors of these genes as a biotechnology strategy of plant protection has not been reported so far (Trapp and Croteau, 2001).

In summary, all these studies suggest that the use of metabolic engineering to achieve resistance against biotic agents represents an alternative technology to the use of expensive fungicide products, bactericides, highly toxic pesticides and that its use would result in an increase in product quality.

Moreover, volatile compounds are important determinants of the perception of aroma and taste of the fruits by humans (Goff and Klee, 2006). Classical plant breeding has been concerned about maximizing attributes such as productivity or vigor, in detriment of other traits as the aroma, and this has led to a gradual losing of flavor and aroma in new varieties of many fruits. Furthermore, it has been proposed that some of the determinant compounds of such traits in fruits are beneficial to health (Bisignano and Saija, 2002). Today, the aroma is considered a quality attribute that should rejoin the new fruit varieties. Again, metabolic engineering is shown as a necessary technology for that purpose. Furthermore, it could allow the production of new combinations of scents in plants with industrial interest for food, perfumery, cosmetics, cleaning, etc.

DETAILED DESCRIPTION OF THE INVENTION

The invention relates to the use of DNA sequences that encode an enzyme with d-limonene synthase activity in antisense or RNAi (RNA interference) configuration for plant genetic transformation of *Citrus* spp. and related genera and species of the Rutaceae family, in order to reduce the accumulation of monoterpene compounds in these plants to achieve systemic resistance or repellency against pests, particularly *Ceratitis capita* Wied., *Tetranychus urticae* Koch., *Panonychus citri* (McGregor), *Dialeurodes citri* Ash, *Parabemisia myricae* (Kuw.), *Trioza erytreae* (Del Guercio), *Coccus hesperidium* L., *Insulapsis gloverii* (Pack), *Chrysomphalus dictyospermi* Morg, *Ceroplastes sinensis* Del Guercio, *Paraleyrodes minei* Laccarino, *Aspidiotus nerii* Bouché, *Parlatarioa pergandei* Const., *Cornuaspis beckii* New., *Diaphorina citri* Kuwayama, *Aonidiella aurantii* (Mask.), *Planococcus citri* (Risso), *Pseudococcus adoidum* L., *P. maritimus* (Ehrhom), *Prays citri* Mill., *Aphys gossypii* Glover, *Mizus persicae* Sulzer, *Aphys spiraecola* (Patch.), *Toxoptera aurantii* (B. de F.), *Aleurothrixus floccosus* Mask, *Icerya purchasi* Mask, *Saissetia oleae* Oliver, cicadelid vectors of CVC (Citrus Variegated Chlorosis) (Family Cicadellidae: Subfamily Cicadellinae), *Anastrepha* spp., *Gymnandrosoma aurantiana* Lima, *Phyllocnistis citrella* Stainton, *Orthezia praelonga* Douglas, *Unaspis citri* (Comstock), *Brevipalpus phoenicis* (Geijskes), or *Phyllocoptruta oleivora* (Ashmead), resistance against pathogens, particularly bacteria such as *Xanthomonas campestris* (Pammel), *Pseudomonas syringae* Van Hall, *Xanthomonas citri* subsp. *citri* (ex Hasse), *Xylella fastidiosa* Wells, *Candidatus Liberibacter* spp., fungi and oomycetes such as *Alternaria citri* Ell. & Pierce, *Alternaria alternata* (Fries) Keissler, *Colletotrichum gloeosporioides* (Penz) Sacc., *Rhizoctonia solani* J. G. Kühn, *Aspergillus niger* P. E. L. van Tieghem, *Guignardia citricarpa* Kiely, *Penicillium italicum* Wehm er, *Botrytis cinerea* Pers.: Fr., *Sphaeropsis tumefaciens* Hedges, *Phytophthora* spp., *Pythium* sp., *Fusarium oxysporum* f.sp. *citri* Timmer, *Penicillium digitatum* (Pers.) Sacc., *Phoma tracheiphila* (Petri) L. A. Kantsch. & Gikaschvili, *Alternaria limicola* E. G. Simmons & M. E. Palm, *Armillaria mellea* (Vahl) P. Kumm., *Phanerochaete salmonicolor* (Berk. & Broome) Jülich, *Colletotrichum acutatum* J. H. Simmonds, *Oidium tingitaninum* J. C. Carter, *Rhizopus stolonifer* (Ehrenb.: Fr.) Vuill., *Pythium ultimum*, *Sclerotinia sclerotiorum* (Lib.) de Bary, *Geotrichum candidum* Link., *Rosellinia* sp., *Elsinoë fawcettii* Bitan. and Jenk., *Elsinoë australis* Bitan. and Jenk., *Pseudocercospora angolensis* (T. Carvalho & O. Mendes) Crous & U. Braun, *Diaporthe citri* Wolf, *Mycosphaerella citri* Whiteside, *Septoria* spp., or nematodes such as *Pratylenchus* spp., *Xiphinema* spp., *Meloidogyne* spp., or *Tylenchulus semipenetrans*, as well as for obtaining new aromatic compounds from tissues of these plants and improve the organoleptic attributes of fruits, flowers and leaves.

DESCRIPTION OF THE DRAWINGS

To complement the description being made and for the purpose of helping to better understand the features of the invention according to a preferred practical embodiment thereof, a set of drawings is attached as an integral part of said description in which the following has been shown with an illustrative and non-limiting character:

FIG. 1.—Shows a precursor nucleotide sequence of an enzyme with d-limonene synthase activity, based on the expression modules that are used to genetically transform plants of *Citrus* spp.

PREFERRED EMBODIMENT OF THE INVENTION

The present invention describes a method for generating resistance against pests and pathogens of citrus trees and related genera through the generation of transgenic plants in which the defense response is activated by means of a reduction in levels of accumulation of certain volatile monoterpenes and sesquiterpenes and an increase in the accumulation of acyclic monoterpene alcohols. This is achieved through downregulation of the accumulation of one or more d-limonene synthase/s of *Citrus* spp. through recombinant expression of an antisense or RNAi construct derived from a precursor gene in plants of *Citrus* spp. and related genera of the Rutaceae family.

Terpenes are the largest group of natural products derived from plants, with over 30,000 known compounds. They are unsaturated hydrocarbons based on an isoprene skeleton (C5H8). In plants, the production of large amounts of terpenes and their subsequent accumulation, emission, or secretion, is associated with the presence of highly specialized anatomical structures, such as the oil glands of the flavedo (outer peel) of citrus fruits.

All terpenes are derived from a five-carbon precursor, the isopentenyl diphosphate (IPP). IPP is formed from acetyl-CoA following the classic acetate/mevalonate pathway in the cytosol and endoplasmic reticulum, while in the plastids it is formed from glyceraldehyde phosphate and pyruvate following the Methylerythritol-4-phosphate pathway (MEP). The isomerization of IPP by IPP isomerase produces the allylic isomer dimethylallyl diphosphate (DMAPP), which is considered the first prenyl diphosphate. DMAPP undergoes condensation with IPP to give the intermediary of ten carbons, the geranyl diphosphate (GPP or GDP) (C10). Repetition of this reaction with the addition of one or two molecules of IPP provides the farnesyl diphosphate (FPP or FDP) (C15) or geranylgeranyl diphosphate (GGPP or GGDP) (C20), respectively. Electrophilic elongation reactions that produce C10, C15 and C20 prenyl diphosphates are catalyzed by prenyltransferases enzymes. These enzymes can use the IPP or DMAPP interchangeably.

The reactions that these compounds undergo (usually cyclizations), catalyzed by terpene synthases, produce a wide variety of terpene compounds. The family of enzymes responsible for the formation of terpenoids from GPP, FPP and GGPP are known as monoterpene, sesquiterpene and diterpene synthases, respectively. Many terpenoids are cyclical, and many contain multiple ring systems, although there are acyclic terpenoids. Terpene synthases that produce cyclic products are also called cyclases. These enzymes have similar properties and contain conserved sequence elements.

Monoterpenes consisting of two isoprene units (C10) are volatile essences of flowers and essential oils of herbs and spices, which can represent up to 5% of plant dry weight. They are isolated by distillation or extraction and have considerable industrial uses in perfumery and flavoring industries. The essential oil glands of citrus fruits are rich in monoterpenes. Of these, d-limonene represents approximately between 90 and 98% of total oils in the peel of sweet orange, sour orange and grapefruit. In citrus flowers, d-limonene is also one of the main components but does not reach the observed concentration of over 90% in the peel of the fruit. It is also cited as an important component in citrus leaves. D-limonene is a monocyclic monoterpene (1-methyl-4-(1-methylethenyl)cyclohexene), whose chemical composition is C10H16. Its molecular weight is 136.24. It is formed from the union of two molecules of isoprene. It is a liquid compound that smells like lemon flavor, insoluble in water and miscible with alcohol. It is commonly found in the form of its d-isomer.

In recent years two d-limonene synthase genes from lemon (CILIMS1 and CILIMS2) (Lücker et al., 2002) and two from satsuma mandarin (CitMTSE1 and CitMTSE2) (Shimada et al., 2004, 2005) have been cloned. Lücker et al. (2004) overexpressed a CILIMS1 along with a γ-terpinene synthase and a β-pinene synthase also from lemon in tobacco through genetic transformation and they achieved a slightly increase in the content of d-limonene and other monoterpenes in flowers of these plants. Endo et al. (2009) overexpressed CitMTSE1 in antisense orientation in *Poncirus trifoliata*, a species related to *Citrus* spp. To overcome the long juvenile period of this plant, they also over-expressed a fast-flowering cassette that allowed them to get fruit after only two years of growth but the plants were usually aberrant. In any case, the use of antisense CitMTSE1 allowed to slightly reduce the levels of d-limonene in the peel of the fruit from *Poncirus trifoliata*. No alteration in the level of accumulation of any other terpene in those fruits was recorded. None of these pioneer works, nor other that used gene precursors of d-limonene synthases incorporated by genetic transformation to other plants, mention any other biological effect resulting from the use of transgenic precursors of d-limonene synthases.

One aspect of the present invention relates to the isolation of nucleic acids that encode enzymes with d-limonene synthase activity, which come from *Citrus* spp. or related to the family Rutaceae, or any other living organism. It is understood that a d-limonene synthase is an enzyme that catalyzes the synthesis of d-limonene. This can be determined by an enzymatic assay well known to those familiar with the art.

Figure 2:
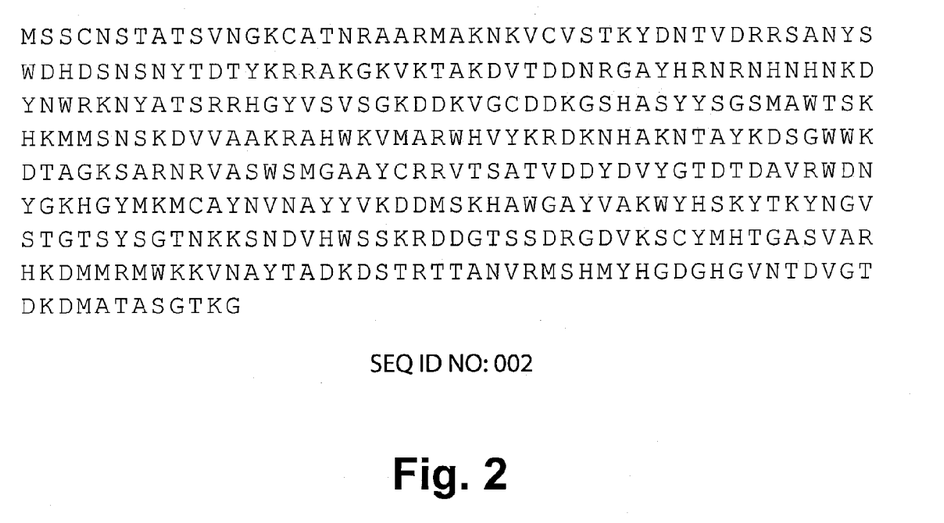
FIG. 2.—Shows a polypeptide sequence of d-limonene synthase product of translation of the nucleotide sequence shown in FIG. 1.

In one part of the present invention, the selected nucleic acid comprise a nucleotide sequence substantially homologous to that presented in FIG. 1, which encodes a polypeptide substantially homologous and functionally equivalent to that shown in FIG. 2, with d-limonene synthase activity.

Preferably, the nucleic acid of the present invention comes from *Citrus* spp. In another embodiment of the invention, a nucleic acid from any living organism that is coding for an enzyme functionally equivalent, i.e. with d-limonene synthase activity, is used.

In this invention, the term nucleic acid refers to deoxyribonucleic acid (DNA), either single or double stranded, isolated from a larger DNA molecule or synthesized from it by PCR, in sufficient quantity and concentration to allow their identification and manipulation using standard procedures in biochemistry. Thus the term DNA includes, for example cDNA, genomic DNA, chemically synthesized DNA, PCR-amplified DNA, and combinations of the above. In general, nucleic acid molecules within the scope of the invention include sequences that hybridize to sequences of the invention under hybridization and wash conditions described above and of 5° C., 10° C., 15° C., 20° C., 25° C., or 30° C. below the melting temperature of the DNA duplex of sequences of the invention, including any range of conditions subsumed within these ranges.

Otherwise, the nucleic acids of the invention comprise a sequence substantially homologous to sequence set out in FIG. 1. In another embodiment, nucleic acids are at least 70%, at least 75%, at least 80%, at least 85%, at least 90% or at least 95% identical to the sequence of FIG. 1, encoding protein sequences with d-limonene synthase activity.

In yet another embodiment, the nucleic acid comprises a contiguous stretch of at least 50, 100, 250, 500, or 750 contiguous nucleotide sequence of FIG. 1. Such contiguous fragments of these nucleotides may also contain at least one mutation so long as the mutant sequence retains the functionality of the original sequence and the capacity to hybridize to these nucleotides under low or high stringency conditions, such as for example, moderate or high stringency conditions. Such a fragment could be derived, for example, from nucleotide (nt) 200 to nt 1800, from nt 800 to nt 1800, from nt 1000 to nt 1800, from nt 200 to nt 1000, from nt 200 to nt 800, from nt 400 to nt 1600, or from nt 400 to nt 1000 of the sequence of FIG. 1.

As described above, polypeptides encoded by the nucleic acids of the invention are encompassed by the invention. The isolated nucleic acids of the invention may be selected from a nucleic acid encoding the polypeptide substantially set out in FIG. 2. In one embodiment of the present invention, the polypeptides are at least 75%, at least 80%, at least 85%, at least 90% or at least 95% identical to the sequence of FIG. 2, and the polypeptides have d-limonene synthase activity.

Due to the characteristic of the genetic code whereby more than one codon can encode the same amino acid, multiple nucleotide sequences can code for the same polypeptide. Such variant DNA sequences can result from genetic drift or artificial manipulation (e.g., occurring during PCR amplification or as the product of deliberate mutagenesis of a native sequence). The present invention thus encompasses any nucleic acid capable of encoding a protein derived from that shown in FIG. 2. Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. In any case, the translated product would retain its d-limonene synthase activity.

In one embodiment of the invention, the cDNA is transcribed into antisense RNA. Antisense RNA is that RNA whose sequence is the reverse complementary of messenger RNA (sense RNA) encoded by a gene. A vector that drive the expression of antisense RNA is one in which the cDNA is placed in "reverse orientation" with respect to the promoter such that the non-coding strand (rather than the coding strand) is transcribed. The expression of antisense RNA can be used to down-modulate the accumulation of the protein encoded by mRNA to which the antisense RNA is complementary. Vectors that produce antisense RNA are used to produce transgenic plants in the present invention.

In another embodiment of the invention, with the intention of further reducing the levels of accumulation of d-limonene synthase, DNA copy is expressed as antisense RNA followed by sense RNA, both fragments separated by an intermediate sequence, preferably an intron, to generate RNA interference (RNAi). This is induced by expressing the RNA transcribed in reverse and in a direct way in the same molecule, so that two complementary forms mate and give rise to a perfectly complementary dsRNA molecule. That molecule is recognized by the DICER complex that digests RNA into small fragments between 20 and 26 nucleotides in length, which in turn are recognized and targeted by the RISC complex to identify the messenger RNA sequence perfectly complementary to these small RNAs. Thus, double-stranded RNAs are generated from the messenger RNA, which are either used as primers to generate new aberrant RNA molecules (recognized by DICER) or are directly degraded by an endonuclease (SLICER) of the RISC complex. RNAi-inducing vectors are also used to genetically transform plants in the present invention. In strategies based on antisense RNA or RNAi, silencing is achieved by the expression of transgenes complementary to the endogenous messenger RNA, so that the expression of endogenous d-limonene synthase genes is reduced or blocked and thus a more or less significant reduction in the level of accumulation and release of d-limonene occurs.

In an embodiment of the invention, the cDNA of the antisense RNA that is used is of at least 50 nucleotides, at least 100 nt, at least 200 nt, at least 500 nt, at least 750 nt, at least 1000 nt, at least 1500 nt or the entire nucleotide sequence reverse complementary to the precursor gene coding for d-limonene synthase.

In another embodiment, cDNA fragment precursors of antisense RNA and sense RNA of the RNAi-generating construct are of at least 50 nucleotides, at least 100 nt, at least 200 nt, at least 500 nt, at least 750 nt, at least 1000 nt, at least 1500 nt or the entire nucleotide sequence (either sense or antisense) of the gene coding for d-limonene synthase.

Figure 3:
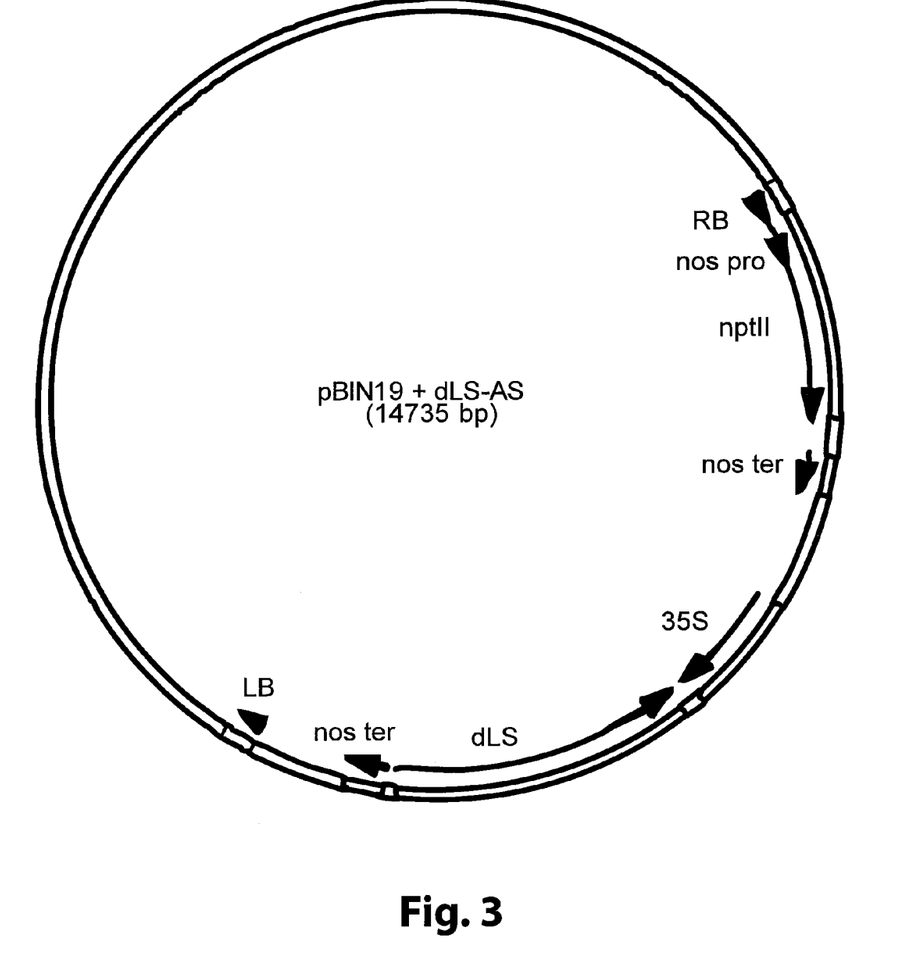
FIG. 3.—Shows the antisense construction, generated from the nucleotide sequence of FIG. 1, in the transformation vector pBIN 19.
Figure 4:
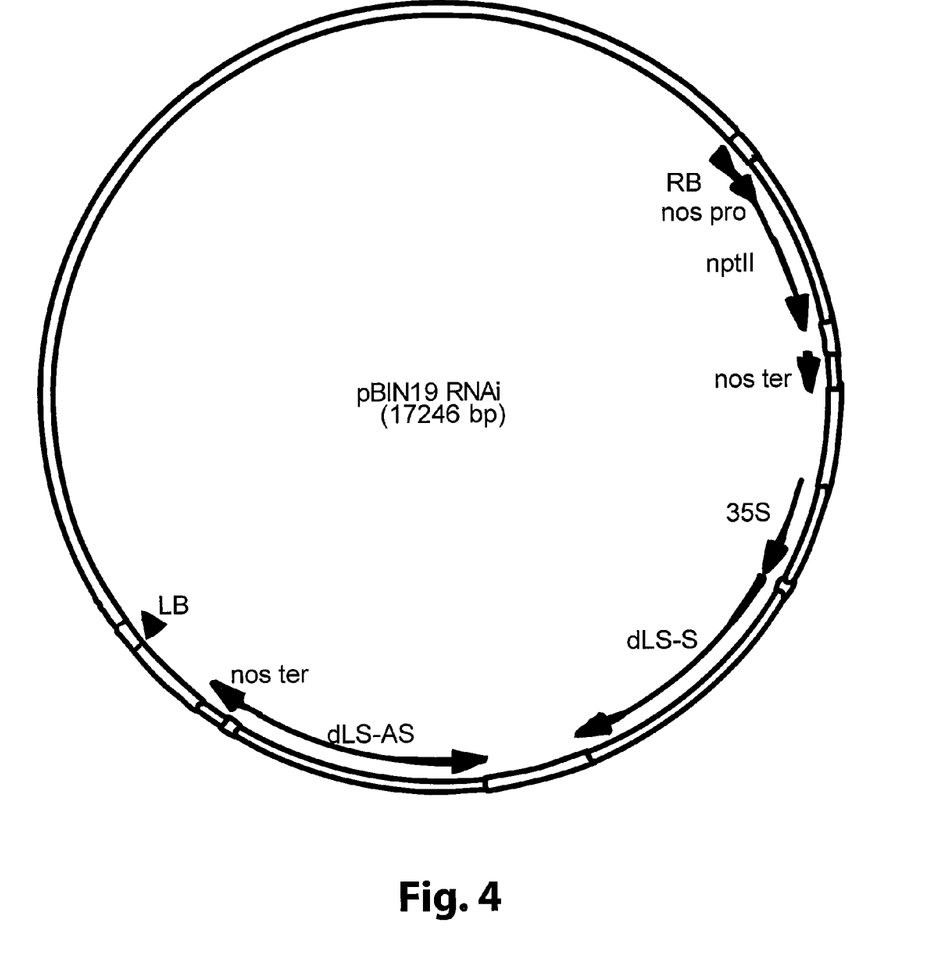
FIG. 4.—Shows the RNAi construction, generated from the nucleotide sequence of FIG. 1, in the transformation vector pBIN 19.

In the present invention, the precursor cDNAs of the constructs for different applications are subcloned into plasmid vectors for genetic transformation of plants, such as those depicted in FIGS. 3 and 4, relating to antisense and RNAi constructs, respectively, shown as an example.

In the invention, the gene constructs are cloned into the transformation vector preferably under the control of regulatory sequences that confer constitutive and high expression, as 35S promoter from the *Cauliflower mosaic* virus (CaMV) and the terminator sequence from the nopaline synthase (NOS) gene or from the 35S, or similar. In another embodiment, the expression of the d-limonene synthase gene (that is intended to be suppressed) is driven by its own promoter and terminator regions. In other preferred embodiments, the expression of the gene is driven by a regulatory region which confers tissue-specific or inducible expression either in fruit or green or floral tissues, known by those familiar with the art.

These vectors and their corresponding expression cassettes of interest are used in the present invention to genetically transform plants. There are numerous procedures for genetically transform plant cells and regenerating whole plants from them. These include (but are not limited to) the transformation mediated by bacteria of the genus *Agrobacterium*, biolistics, microinjection, electroporation, mediated by plant viruses, mediated by silicon carbide fibers, by infiltration of floral tissues, mediated by liposomes, polyethylene glycol-mediated and mediated by other bacteria, among others.

In the preferred implementation of the present invention, *Agrobacterium tumefaciens* is used as a vector for transformation, without discarding any of the other possible systems of genetic modification. Genetic transformation of plants mediated by *Agrobacterium tumefaciens* is the most common method for genetic transformation of citrus and related genera of the Rutaceae family.

*A. tumefaciens* uses typically transformation as a system for inserting specific fragments of its own DNA into the genome of plant cells. In such DNA there are genes involved in biosynthesis of plant hormones, so its expression in cells leads to tumor formation in infected areas. Genes that are transferred reside in the so-called T-DNA, which is in turn part of a megaplasmid called Ti (tumor-inducing) plasmid. It is possible to replace the oncogenic T-DNA from the Ti plasmid of *A. tumefaciens* through genetic engineering by another T-DNA in which the genes of interest that are intended to be integrated into plant cells are cloned. Thus, the disarmed bacterium is used as a vector to incorporate foreign genes into plant cells. From those transformed cells it is possible to regenerate whole plants using standard in vitro regeneration systems, well known to those familiar with the art.

In the invention, protoplasts, cell suspensions or explants from leaves, internodes, nodes, cotyledons, seeds, epicotyls, flowers, roots, fruit segments, or any other organ or tissue of the plant are used for genetic transformation.

In the invention, the genetic constructs of interest are used to genetically transform plants of sweet orange, of mandarin, of clementine, of satsuma, of sour orange, of lemon, of lime, of pummelo, of citron, of alemow, of grapefruit or any other species of the genus *Citrus*, of *Poncirus trifoliata*, of *Fortunella* spp., or any other Rutaceae, of citrange, of citrumelo, of tangelo, of tangor, or any other hybrid belonging to *Citrus* or *Citrus* and Rutaceae.

In the invention, the procedures of the Spanish patent number 9700491/X (U.S. Pat. No. 6,103,955) and Peña et al. (2008) for genetic transformation of adult material are preferably used.

Thus, transgenic plants, preferably mature ones, are generated and characterized by conventional molecular assays as PCR, Southern blot, Northern blot and similar ones. In the invention, the analysis by gas chromatography—mass spectrometry is carried out from different tissues obtained from transgenic plants such as leaves, petals, fruit flavedo, fruit pulp and similar tissues, or tissues are analyzed by any other similar technique that allows to determine the change in the content and release of volatile terpenes in the tissues of the transgenic plants.

In the invention, the use of antisense and RNAi strategies leads to a reduction in the accumulation of a d-limonene synthase transcript and of transcripts from genes sufficiently homologous to it. This leads to a drastic reduction in the accumulation of enzymes for d-limonene synthase activity. In the present invention, it occurs a decrease in the synthesis, accumulation and release of d-limonene and other cyclic monoterpenes such as sabinene, delta-3-carene, beta-myrcene, ocimene, alpha-terpinolene, limonene oxides, among others and sesquiterpenes such as alpha-copaene, beta-cubenene, germacrene-D, beta-elemene, caryophyllene, beta-farnesene, alpha-farnesene, and beta-sinensal among others. In the invention, the decrease in the accumulation of d-limonene leads to an increase in the accumulation and emission of acyclic monoterpene alcohols such as beta-citronellol, nerol and geraniol and esters such as geranyl acetate and others.

In the invention, the alteration in the accumulation and emission of terpene compounds makes transgenic plants and/or their fruits repellent or resistant to insect pests such as *Ceratitis capitata* Wied., *Tetranychus urticae* Koch., *Panonychus citri* (McGregor), *Dialeurodes citri* Ash, *Parabemisia myricae* (Kuw.), *Trioza erytreae* (Del Guercio), *Coccus hesperidium* L., *Insulapsis gloverii* (Pack), *Chrysomphalus dyctiospermi* Morg, *Ceroplastes sinensis* Del Guercio, *Paraleyrodes minei* Laccarino, *Aspidiotus nerii* Bouché, *Parlatarioa pergandei* Const., *Cornuaspis beckii* New., *Diaphorina citri* Kuwayama, *Aonidiella aurantii* (Mask.), *Planococcus citri* (Risso), *Pseudococcus adoidum* L., *P. maritimus* (Ehrhom), *Prays citri* Mill., *Aphys gossypii* Glover, *Mizus persicae* Sulzer, *Aphys spiraecola* (Patch.), *Toxoptera aurantii* (B. de F.), *Aleurothrixus floccosus* Mask, *Icerya purchasi* Mask, *Saissetia oleae* Oliver, cicadellid vectors of CVC (Family Cicadellidae: Subfamily Cicadellinae), *Anastrepha* spp., *Gymnandrosoma aurantiana* Lima, *Phyllocnistis citrella* Stainton, *Orthezia praelonga* Douglas, *Unaspis citri* (Comstock), *Brevipalpus phoenicis* (Geijskes), or *Phyllocoptruta oleivora* (Ashmead), resistance against pathogens, particularly bacteria such as *Xanthomonas campestris* (Pammel), *Pseudomonas syringae* Van Hall, *Xanthomonas citri* subsp. *citri* (ex Hasse), *Xylella fastidiosa* Wells, Candidatus *Liberibacter* spp., fungus and oomycetes such as *Alternaria citri* Ell. & Pierce, *Alternaria alternata* (Fries) Keissler, *Colletotrichum gloeosporioides* (Penz) Sacc., *Rhizoctonia solani* J. G. Kühn, *Aspergillus niger* P. E. L. van Tieghem, *Guignardia citricarpa* Kiely, *Penicillium italicum* Wehmer, *Botrytis cinerea* Pers.: Fr., *Sphaeropsis tumefaciens* Hedges, *Phytophthora* spp., *Pythium* sp., *Fusarium oxysporum* f.sp. *citri* Timmer, *Penicillium digitatum* (Pers.) Sacc., *Phoma tracheiphila* (Petri) L. A. Kantsch. & Gikaschvili, *Alternaria limicola* E. G. Simmons & M. E. Palm, *Armillaria mellea* (Vahl) P. Kumm., *Phanerochaete salmonicolor* (Berk. & Broome) Jülich, *Colletotrichum acutatum* J. H. Simmonds, *Oidium tingitaninum* J. C. Carter, *Rhizopus stolonifer* (Ehrenb.: Fr.) Vuill., *Pythium ultimum, Sclerotinia sclerotiorum* (Lib.) de Bary, *Geotrichum candidum* Link., *Rosellinia* sp., *Elsinoë fawcettii* Bitan. and Jenk., *Elsinoë australis* Bitan. and Jenk., *Pseudocercospora angolensis* (T. Carvalho & O. Mendes) Crous & U. Braun, *Diaporthe citri* Wolf, *Mycosphaerella citri* Whiteside, *Septoria* spp., or nematodes such as *Pratylenchus* spp., *Xiphinema* spp., *Meloidogyne* spp., or *Tylenchulus semipenetrans*. In another embodiment of the invention, the decrease in the accumulation of d-limonene leads to an increased production of certain acyclic monoterpene alcohols creating new blends of essential oils that have industrial, pharmaceutical and medical interest.

EXAMPLES OF THE INVENTION

The figures, percentages, specific ingredients and organisms listed below should be considered only as examples, without limiting the scope and claims of the patent. All scientific terms mentioned above have the same meaning as commonly understood by one of ordinary skill in the art to which this invention belongs.

Materials

The *Citrus* material used in the examples described below was obtained from the *Citrus* germplasm bank of the IVIA (Instituto Valenciano de Investigaciones Agrarias, Moncada, Valencia, Spain).

Example 1

Construction of Expression Cassettes

Total RNA was extracted from 2 g of fruit flavedo from sweet orange, using the procedure described by Rodrigo et al. (2004) and as detailed below:

Add 10 mL of extraction buffer (200 mm Tris-HCl pH8, 400 mM NaCl, 50 mM EDTA pH8, 2% Sarkosyl, 1% PVP-40) to 2 grams of flavedo tissue, 100 µL of β-mercaptoethanol and 5 mL of phenol (balanced with Tris) in a centrifuge tube. Vortex and incubate for 15 minutes at 65° C. Add 5 mL of cloforom:isoamyl alcohol (24:1). Centrifuge at 4,500 rpm for 20 minutes at 4° C. Recover the aqueous phase into a new tube. Add again 5 mL of phenol and 5 mL of chloroform: isoamyl alcohol (24:1). Centrifuge at 4,500 rpm for 20 minutes at 4° C. Recover the aqueous phase again and transfer to a new centrifuge tube. Add 1.5 volumes of 100% ethanol, mix and centrifuge at 15,000 rpm for 15 minutes at 4° C. Remove the supernatant and wash the pellet with 5 mL of 70% ethanol (cold). Centrifuge at 15,000 rpm for 5 min at 4° C. Remove the supernatant and resuspend the pellet in 7.5 mL of TESA (10 mM Tris-HCl pH8, 5 mM EDTA, 0.1% Sarkosyl). Incubate 15 minutes in water bath at 65° C. to complete resuspension. Add 7.5 mL of sterile Milli-Q water. Centrifuge at 8,000 rpm for 5 min at 4° C. Transfer supernatant to a new centrifuge tube. Add 0.33 volumes of lithium chloride 12M and incubate at 4° C. overnight. Centrifuge at 15,000 rpm for 30 minutes at 4° C. Remove the supernatant and wash the pellet with 1.5 mL of 70% ethanol. Centrifuge at 13,000 rpm for 5 minutes. Resuspend the pellet with 1 mL of sodium acetate 3M pH 6. Centrifuge at 15,000 rpm for 15 minutes at room temperature. Wash the pellet with 0.5 mL of 70% ethanol. Centrifuge at 15,000 rpm for 5 minutes at room temperature. Dry the pellet and resuspend in 100 µL of sterile milli-Q water.

Subsequently, RNA was purified using a RNA purification kit and an on-column DNase treatment was performed to avoid DNA contamination of samples.

Figure 5:
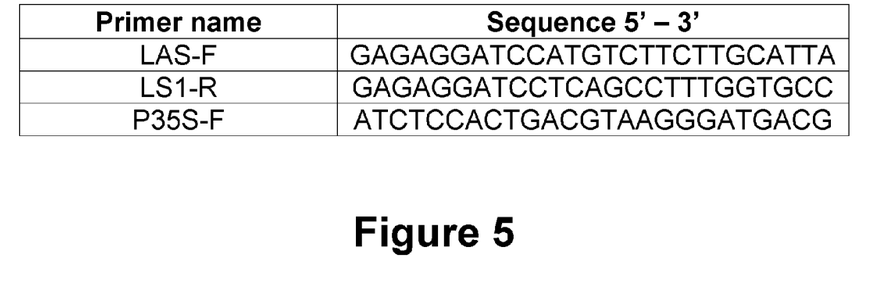
FIG. 5.—Shows sequences of primers used to clone a gene precursor of a d-limonene synthase from sweet orange.
Figure 6:
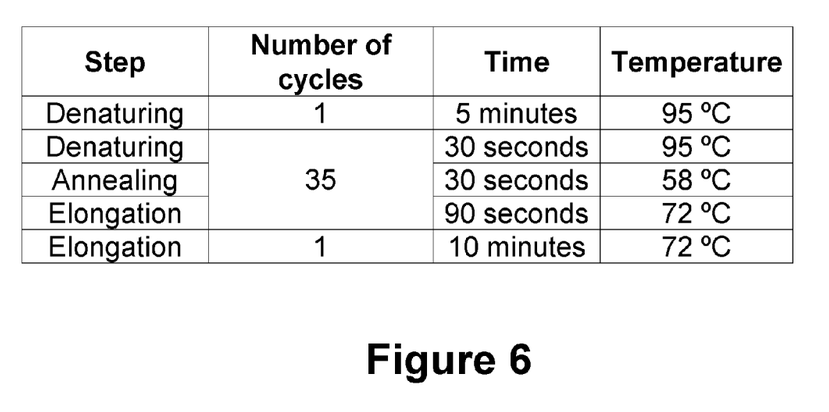
FIG. 6.—Shows the PCR conditions used to clone a gene precursor of a d-limonene synthase from sweet orange.

From DNase-treated RNA, reverse transcription of RNA was performed to obtain the cDNA. For cloning of d-limonene synthase from sweet orange, specific primers were designed (LAS-F and LS1R) which added a BamHI restriction site to facilitate subsequent cloning into a binary plasmid. The primers used are described in FIG. 5. As reverse primer the LS1-R was used. For amplification of d-limonene synthase, we used PCR (polymerase chain reaction) in which primers LAS-F and LS1-R and the conditions set out in FIG. 6 were used. This fragment was cloned into the binary plasmid pBIN 19 by digestion with the enzyme BamHI between the terminator sequences of the nopaline synthase gene (NOS) and 35S promoter from the *Cauliflower mosaic* virus, previously introduced into the plasmid. The correct orientation of the fragments was assessed by sequencing.

To synthesize the construction generating RNAi, an intron sequence, the DNA copy of the antisense and sense DNA copy were cloned sequentially in an intermediate plasmid pGEM-T.

Example 2

Genetic transformation of *Citrus* with *Agrobacterium tumefaciens* carrying the constructs of interest, transgene precursors of a d-limonene synthase gene in antisense and RNAi configuration. Regeneration of whole transgenic plants from transformed cells and tissues.

The genetic constructs of interest were cloned into the transformation vector pBIN 19 under the control of 35S promoter from the *Cauliflower mosaic* virus (CaMV) and the nopaline synthase (NOS) gene terminator. Besides the expression cassette of interest, the T-DNA contained the neomycin phosphotransferase II (nptII) transgene, which confers resistance to kanamycin to transformed cells, under the control of the NOS promoter and terminator. Plasmids of interest pBIN19/AS and pBIN19/RNAi were introduced into *Agrobacterium tumefaciens* strain EHA 105 (derived disarmed from strain A281) by electroporation.

As starting plant material we used adult sweet orange buds grafted onto vigorous juvenile rootstocks in the greenhouse. Once sprouted, stems were cut for sets of about 30-40 cm in length, they were stripped of leaves and thorns and subsequently washed with soap and 2% of sodium chloride. In sterile conditions, internode segments of 1 cm-long were used as explants for transformation. About 40 explants per plate were plunged in 30 mL culture of *A. tumefaciens* for 15 minutes with agitation in inoculation medium (4.3 $gL^{-1}$ Murashige and Skoog salts (1962), 10 $mLL^{-1}$ of vitamin solution (100 $mgL^{-1}$ of myo-inositol, 0.2 $mgL^{-1}$ of thiamine-HCl, 1 $mgL^{-1}$ pyridoxine-HCl, 1 $mgL^{-1}$ nicotinic acid, 30 $gL^{-1}$ sucrose, pH 5.7). After that time, explants were dried on sterile filter paper. Some explants were inoculated in inoculation medium without bacteria to control that shoot regeneration occurred normally. After the inoculation time, about 40 explants were placed in cocultivation medium (inoculation medium plus 2 $mgL^{-1}$ of 2.4 dichlorophenoxyacetic acid (2,4-D), 2 $mgL^{-1}$ indoleacetic acid (IAA), 1 $mgL^{-1}$, 2-isopentenyl-adenine (2, iP), 8 $gL^{-1}$ agar, pH 5.7) and incubated in semi-darkness conditions for 3 days at 26° C. (10 $\mu Em^{-2}s^{-1}$, 16 h photoperiod). After cocultivation, about 10 explants per plate were transferred to selection medium (inoculation medium plus 1.3 $mgL^{-1}$ of 6-benzylaminopurine (BAP), 10 $gL^{-1}$ agar, pH 5.7, 250 $mgL^{-1}$ cefotaxime and 250 $mgL^{-1}$ of vancomycin and kanamycin sulfate at 100 $mgL^{-1}$). Explants were kept in darkness for a period of approximately 4 weeks at 26° C., to allow the formation of callus at the cut ends of the explants. They were subsequently transferred to a growth chamber with a photoperiod of 16 h, 45 $\mu Em^{-2}s^{-1}$ light and 26° C. Regenerating buds began to arise normally about 7 to 9 weeks after cocultivation. The new shoots were checked by PCR analysis (Polymerase Chain Reaction) with specific primers of the transgene (P35S-F, LAS-F for checking the construction in antisense and RNAi, FIG. 5 and FIG. 6), which allowed distinguishing positive from negative buds.

Positive shoots were grafted on Troyer or Carrizo citrange rootstocks, from in vitro germinated-seeds. These grafts were transferred to growth chamber at 25° C., 16 h photoperiod, 45 $\mu Em^{-2}s^{-1}$ light. The scions developed 2 to 3 expanded leaves 3 to 4 weeks after grafting. They were then re-grafted onto vigorous rootstocks in the greenhouse under shade mesh and covered with a plastic bag during the first three weeks, allowing a rapid acclimatization and development of plants. At approximately 4 to 5 weeks of being grafted in the greenhouse, each plant was transferred to non-mesh zone where they continued its growth.

Plants were subsequently characterized by Southern blot and Northern blot analysis to confirm the stable integration and determine the integration pattern of transgenes in each independent transgenic line and the accumulation level of transcripts, respectively.

Example 3

Change in the profile of accumulation of volatile terpenes in transgenic plants.

Diverse analyses by gas chromatography—mass spectrometry of different tissues obtained from transgenic plants (leaves, petals, pulp vesicles and fruit flavedo) were conducted. The use of antisense and RNAi strategies led to generating independent transgenic lines in which a reduction in transcript accumulation of the d-limonene synthase gene and in transcripts of related (homologous) genes was observed. This led to a drastic reduction in the accumulation of enzymes with d-limonene synthase activity. In these transgenic plants, there was a decrease in the synthesis, accumulation and release of d-limonene of about 50 times less than control lines and in other monoterpenes such as sabinene, delta-3-carene, beta-myrcene, ocimene, alpha-terpinolene, limonene oxide, sabinene hydrate, linalyl propionate, perilla aldehyde, octanal, nonanal, decanal or undecanal, isopiperitenone, and sesquiterpenes such as alpha-copaene, beta-cubenene, germacrene-D, beta-elemene, caryophyllene, beta-farnesene, alpha-farnesene, muurolene, elemol or beta-sinensal in fruits.

The decrease in the accumulation of d-limonene led to an increase in the accumulation and emission of acyclic monoterpene alcohol such as beta-citronellol, nerol, geraniol and esters such as geranyl acetate or neryl acetate.

Example 4

Post-harvest fungus infection, in order to demonstrate the antifungal activity of genetically transformed plants carrying d-limonene synthase antisense and RNAi constructs.

In challenge infection experiments with *Penicillium digitatum* and *P. minioluteum*, citrus fruits from Navelina and Pineapple sweet orange harvested in two consecutive years were used. All fruits were collected before any post-harvest treatment and processed the same day of collection. Fruits that were neither damaged nor rotten were selected and were disinfected by immersion in a bleach solution (0.5% NaCl) for 1 minute. Then, fruits were rinsed with water and dried with paper.

Fruits were infected with the fungus *P. digitatum* (Pers.: Fr) Sacc. (PD), the causal agent of green rot of citrus fruits during post-harvest. Strain NAV-7 from the laboratory of post-harvest technology of IVIA was used. Furthermore, we employed other citrus nonpathogenic fungus, *Penicillium minioluteum* (PM), obtained in the same laboratory, to verify the absence of infection in fruits.

The fungus *P. digitatum* ($10^4$ spores/mL) was inoculated in three equidistant points from the equator zone of the fruit using the classic citrus inoculation rod dipped in a spore suspension. The fungus *P. minioluteum* ($10^4$ spores/mL) was inoculated in eight points of the peel using the same methodology. Inoculated fruit remained in separate holes of boxes without sealing (1 tray per treatment) and incubated in a thermostatic chamber at 20° C. After three days and up to approximately 14 days after inoculation, the diameter of lesions in each fruit was measured and the area under disease progress (AUDPC) was estimated. To determine the severity of the disease, only injuries with symptoms were considered. For the analysis, the percentage of infected and sporulated wounds was also considered. Data for incidence and severity of the lesions corresponded to the average value of at least 15 fruits with 3 wounds per fruit. The data analysis was performed using the statistical package 'Statgraphics Plus 5.1' (Manugistics, Inc.) using analysis of variance (ANOVA). A study of the homogeneity of variance and, if it was homogeneous, LSD test was used, considering significant differences with $p<0.05$.

The results indicated significant differences for incidence between treatments of genetically transformed lines with d-limonene synthase antisense or RNAi constructions and control lines. There was a substantial reduction in the appearance of injury symptoms in antisense and RNAi lines compared to controls.

Example 5

Plant pathogenic bacterium challenge infection, in order to demonstrate the antibacterial activity of genetically transformed plants with d-limonene synthase antisense and RNAi constructs.

In experiments of challenge infection with *Xanthomonas citri* subsp. *citri*, fruits were used in two different maturation stages. We used Navelina and Pineapple orange varieties. All fruits were collected before any post-harvest treatment and processed the same day of collection. Intact fruits were selected and disinfected by washing in a solution of 70% alcohol and dried with paper.

In the first assay, green fruits of about 5 to 6 cm in diameter were used, while for the second assay, color-changing fruits of about 7 to 8 cm in diameter were used. The Brazilian isolate of *X. citri* (strain 306) was used to inoculate fruits at a concentration of $10^6$ cells/mL. Five to seven inoculation points per fruit were carried out with an awl and inoculation was performed by syringe pressure. The fruits were incubated in a chamber with controlled conditions at a temperature of 30° C. and 55% RH. The diameter of halo and the formation of canker wounds were evaluated.

The results indicated significant differences for incidence between treatments with genetically transformed and control lines. There was a significant reduction in symptoms in antisense and RNAi lines compared to controls.

Example 6

Tests against insects, to demonstrate the repellency activity of volatiles from genetically transformed plants with d-limonene synthase antisense and RNAi constructs. Appropriate biological tests were carried out taking Mediterranean fruit fly (*Ceratitis capitata* Wied.) as an example. Experiments with cages.

In studies performed with the Mediterranean fruit fly (*Ceratitis capitata* Wied.), sweet orange fruiting plants were used. Only one fruit per plant in color break stage was left in each tree. Navelina orange plants, both non-transformed and genetically transformed with either d-limonene synthase antisense or RNAi constructs, propagated in the greenhouse were used. A control plant in which an apple was tied was also included in each test in order to use it as an egg laying control of *Ceratitis*. Plants were isolated in specific cages in the greenhouse each with 40 males and 40 females of 5 to 6 days-old *C. capitata* flies reared in laboratory. Flies were maintained three days in cages with food and water for allowing oviposition. After 3 days, fruit was cut and let in an incubation chamber for further development of pupae. We evaluated the influx of flies, the number of oviposition sites per fruit, the number of pupae per fruit and the number of adults emerged (both males and females).

Tests showed a preference of the medfly to the aroma of fruits from non-transformed plants compared to transgenic fruits with dramatically reduced levels of the monoterpene d-limonene and other terpenes and increased levels of acyclic monoterpenes.

Example 7

Tests against insects, to demonstrate the repellency activity of volatiles from genetically transformed plants carrying d-limonene synthase antisense and RNAi constructs. Appropriate biological tests were carried out taking Mediterranean fruit fly (*Ceratitis capitata* Wied.) as an example.
Wind Tunnel Experiments.

In studies performed with the Mediterranean fruit fly (*Ceratitis capitata* Wied.), sweet orange cut fruits were used in color break stage. Navelina orange plants, both non-transformed and genetically transformed with either d-limonene synthase antisense or RNAi constructs, propagated in the greenhouse were used. Several assays were conducted in a wind tunnel, with non-transformed control and transgenic fruit. In each assay, 50 males of 5 to 6 days-old *C. capitata* flies reared in laboratory were released. Medfly males remained 30 minutes in the wind tunnel. Their behavior was evaluated by the number of flies landing in each fruit every 5 minutes.

Tests showed a preference of the medfly to the aroma of fruits from non-transformed plants compared to transgenic fruits with dramatically reduced levels of the monoterpene d-limonene and other terpenes and increased levels of acyclic monoterpenes.

Example 8

Flavor Improvement

The modification of the organoleptic attributes of citrus fruits, leaves and flowers was confirmed in several analyses by gas chromatography—mass spectrometry of sweet orange plants transformed with d-limonene synthase antisense and RNAi constructs.

The use of d-limonene synthase antisense and RNAi constructs resulted in a drastic variation of the volatile profile of fruits from sweet orange-transformed plants. Levels of d-limonene were reduced about 50 times and also levels of other monoterpenes such as sabinene, delta-3-carene, beta-myrcene, ocimene, alpha-terpinolene, limonene oxide, sabinene hydrate, linalyl propionate or isopiperitenone. Likewise, a decrease in levels of other monoterpenes in the group of aldehydes such as perilla aldehyde, octanal, nonanal, decanal or undecanal and sesquiterpenes as alpha-copaene, beta-cubenene, germacrene-D, beta-elemene, caryophyllene, beta-farnesene, alpha-farnesene, muurolene, elemol or beta-sinensal was recorded. Moreover, there was an increase in the content of acyclic monoterpene alcohols, such as beta-citronellol, nerol, geraniol, and esters such as geranyl acetate.

These features gave rise to plants with a completely altered volatile profile and led to obtaining a new aromatic product for the market. The increase in alcohols, typical of floral fragrances, resulted in obtaining products more appealing to the consumer as it was revealed by flavor panels performed at IVIA and IATA (Instituto de Agroquímica y Tecnología de los Alimentos), and with potential medicinal properties.

Example 9

Obtaining new flavoring products for possible use in perfumes, flavorings, cleaning, pharmaceutical and medical industries.

The modification of the organoleptic attributes of fruits, leaves and flowers of transgenic citrus trees carrying the constructs in antisense or RNAi resulted in the production of essential oil compositions different from those marketed to date coming from citrus tissues. The distillation of essential oils from these transgenic plants gave rise to new products that could be combined perfectly with the components generally used in perfumes and other products. The new compositions can be used directly in the perfumery industry or used for cosmetic preparations such as creams, lotions, colognes, sprays, soaps, mouth care agents, and to improve product odor such as softeners for laundry, cleaning and disinfecting agents. They can also be used in food industry as flavorings and preservatives in beverages and foods. The increase in the content of some specific terpene compounds with potential medicinal properties permits to propose the use of derived essential oils in pharmaceutical preparations.

The embodiments and examples illustrated and discussed in this specification are intended only to teach those skilled in the art the best way known to the inventors to make and use the invention. The above-described embodiments of the invention may be modified or varied, without departing from the invention, as easily appreciated by those skilled in the art in light of the above teachings. Accordingly, all expedient modifications readily attainable by one of ordinary skill in the art from the disclosure set forth herein, or by routine experimentation therefrom, are deemed to be within the spirit and scope of the invention as defined by the appended claims.

REFERENCES

Aharoni, A., Giri, A. P., Deuerlein, S., Griepink, F., Kogel, W., Verstappen, F. W. A., Verhoeven, H. A., Jongsma, M. A., Schwab, W. & Bouwmeester, H. J. Terpenoid metabolism in wild-type and transgenic *Arabidopsis* plants. Plant Cell 15, 2866-2884 (2003).

Arimura, G., Ozawa, R., Shimoda, T., Nishioka, T., Boland, W. and Takabayashi, J. Herbivory-induced volatiles elicit defence genes in lima bean leaves. Nature 406, 512-515 (2000).

Bisignano, G. and Saija, A. The biological activity of citrus oils. Citrus. Medicinal and aromatic plants-Industrial profiles. (Dugo, G. and Di Giacomo, A. Eds.). Chapter 28, pp. 602-630. Taylor & Francis Group, Florida, USA (2002).

De Moraes, C. M., Mescheer, M. C. and Tumlinson, J. H. Caterpillar-induced nocturnal plant volatiles repel nonspecific females. Nature 410, 577-580 (2001).

Degenhardt, J., Hiltpold, I., Köllner, T. G., Frey, M., Gieri, A., Gershenzon, J., Hibbard, B. E., Ellersieck, M. R. and Turlings, T. C. J. Restoring a maize root signal that attracts insect-killing nematodes to control major pest. PNAS 106 (32), 13213-13218 (2009).

Endo, T., Shimada, T., Fujii, H., Nishikawa, F., Sugiyama, A., Nakano, M., Shimizu, T., Kobayashi, Y., Araki, T., Pěna, L. and Omura, M. Development of a ciFT co-expression system for functional analysis of genes in citrus flowers and fruit. J. Japan. Soc. Hort. Sci 78 (1), 74-83 (2009).

Gershenzon, J. and Dudareva, N. The function of terpene natural products in the natural world. Nat. Chem. Biol. 3, 408-414 (2007).

Goff, S, and Klee, H. Plant volatile compounds: sensory cues for health and nutritional value?. Science 311, 815-819 (2006).

Kappers, I. F., Aharoni, A., van Herpen, T. W. J. M., Luckerhoff, L. L. P., Dicke, M. and Bouwmeester, H. J. Genetic engineering of terpenoid metabolism attracts bodyguards to *Arabidopsis*. Science 309, 2070-2072 (2005).

Kessler, D., Gase, K. and Baldwin, T. Field experiments with transformed plants reveal the sense of floral scents. Science 321, 1200-1202 (2008).

Lücker, J., El Tamer, M. K., Schwab, W., Verstappen, F. W. A., van der Plas, L. H. W., Bouwmeester, H. J., Verhoeven, H. A. Monoterpene biosynthesis in lemon (Citrus limon)—cDNA isolation and functional analysis of four monoterpenes synthases. Eur. J. Biochem. 269, 3160-3171 (2002).

Lücker, J., W. Schwab, B. V. Hautum, J. Blass, L. H. W. van der Plas, H. J. Bouwmeester and H. A. Verhoeven. Increased and altered fragance of tobacco plants after metabolic engineering using three monoterpene synthases from lemon. Plant Physiol. 134: 510-519 (2004).

Peña, L., Cervera, M., Fagoaga, C., Romero, J., Ballester, A., Soler, N., Pons, E., Rodriguez, A., Peris, J., Juárez, J. and Navarro, L. Citrus. Compendium of Transgenic Crop Plants: Transgenic Tropical and Subtropical Fruits and Nuts, Volume 5. (Kole, C. and Hall, T. C. Eds.), Chapter 1, pp. 1-62. Wiley-Blackwell Publishing, Oxford, UK (2008).

Rodrigo, M. J., Marcos, J. F. and Zacarias, L. Biochemical and molecular analysis of carotenoid biosynthesis in flavedo of orange (*Citrus sinensis* L.) during fruit development and maturation. J. Agric. Food Chem. 52, 6724-6731 (2004).

Schnee, C., Köllner, T. G., Held, M., Turlings, T. C. J., Gershenzon, J. & Degenhardt, J. The products of a single maize sesquiterpene synthase form a volatile defense signal that attracts natural enemies of maize herbivores. Proc. Natl. Acad. Sci. USA 103, 1129-1134 (2006).

Shimada, T., Endo, T., Fujii, H., Hara, M., Ueda, T., Kita, M., Omura, M. Molecular cloning and functional characterization of four monoterpenes synthase genes from *Citrus unshiu* Marc. Plant Sci. 166, 49-58 (2004).

Shimada, T., Endo, T., Fujii, H., Omura, M. Isolation and characterization of a new d-limonene synthase gene with a different expression pattern in *Citrus unshiu* Marc. Sci. Hortic. 105, 507-512 (2005).

Trapp, S. & Croteau, R. Defensive resin biosynthesis in conifers. Ann. Rev. Plant Physiol. and Plant Mol. Biol. 52, 689-724 (2001).

Wu, S., Schalk, M., Clark, A., Miles, R. B., Coates, R. & Chapell, J. Redirection of cytosolic or plastidic isoprenoid precursors elevates terpene production in plants. Nat. Biotech. 24, 1441-1447 (2006).

What is claimed is:

1. A method for generating resistance against diseases affecting wildtype citrus fruits and caused by at least one of *Penicillium digitatum, Penicillium miniolutem, Xanthomonas citri*, and *Ceratitis capitata* Wied., comprising:
genetically transforming a plant of a *Citrus* spp., by introducing a transgene encoding at least an antisense RNA having a sequence corresponding to a d-limonene synthase gene configured to trigger RNA silencing of at least an endogenous messenger RNA encoding a polypeptide with d-limonene synthase activity; and
performing at least one assay to determine whether a reduction in d-limonene synthase activity and an accumulation of endogenous d-limonene to levels that trigger a plant defense response in a citrus fruit of the transformed plant against at least one of *Penicillium digitatum, Penicillium miniolutem, Xanthomonas citri*, and *Ceratitis capitata* Wied. has been achieved.

2. The method of claim 1, wherein the transgene has a sequence corresponding to a *Citrus* spp. d-limonene synthase gene encoding an enzyme with d-limonene synthase activity isolated from a wildtype *Citrus* spp.

3. The method of claim 1, wherein the transgene comprises a sequence corresponding to at least one of: an endogenous wildtype *Citrus* spp. d-limonene synthase gene having at least one deletion and at least a portion of a wildtype *Citrus* spp. d-limonene synthase gene having at least one insertion, so that the expression of the polypeptide with d-limonene synthase activity is reduced or blocked.

4. The method of claim 1, further comprising producing citrus peel-derived bioethanol from the citrus fruit of the transformed plant.

5. The method of claim 1, wherein the expression of the transgene is driven by a strong constitutive promoter to reduce levels of d-limonene synthase in all cells of the transformed plant.

6. The method of claim 1, wherein the transgene is derived from a wildtype organism, and expression of the transgene is driven by promoter and terminator regions of the d-limonene synthase gene from the wildtype organism.

7. The method of claim 1, wherein the transgene is incorporated into the plant of a *Citrus* spp. through genetic transformation of cells or tissues and regeneration of a whole *Citrus* spp. plant through organogenesis or through somatic embryogenesis.

8. The method of claim 1, wherein the reduction in levels of d-limonene increases expression of genes related to immunity against citrus fruit pests and pathogens.

9. The method of claim 1, wherein the accumulation of d-limonene in the citrus fruit is reduced by 50 times as compared to a non-transformed plant of the same *Citrus* spp.

10. The method of claim 1, wherein the accumulation of d-limonene in the citrus fruit is reduced by at least 50 times as compared to a non-transformed plant of the same *Citrus* spp.

11. The method of claim 1, wherein the transgene has a sequence of a d-limonene synthase wildtype gene encoding an enzyme with d-limonene synthase activity isolated from a plant belonging to the Rutaceae family.

12. The method of claim 1, wherein the transgene comprises a sequence corresponding to a portion of the endogenous wildtype d-limonene synthase gene of the plant.

13. The method of claim 1, wherein the transgene comprises a DNA sequence of at least 50 nucleotides having at least 95% antisense sequence homology to a corresponding portion of SEQ ID NO. 1.

14. The method of claim 1, wherein the expression of the transgene is driven by tissue-specific or inducible regulator regions.

15. The method of claim 1, further comprising extracting at least one of a flavor and a scent from juice derived from the transformed plant.

16. The method of claim 1, wherein the d-limonene synthase transgene comprises a copy of a complete endogenous wildtype d-limonene synthase gene, so that the expression of the endogenous d-limonene synthase gene is reduced or blocked.

17. The method of claim 1, wherein the reduction in accumulation of d-limonene is associated with an increase in accumulation of acyclic monoterpene alcohols.

18. A method for reducing d-limonene in citrus fruit, comprising:

genetically transforming a plant of a *Citrus* spp., by introducing a transgene encoding at least an antisense RNA having a sequence corresponding to a d-limonene synthase gene configured to trigger RNA silencing of at least an endogenous messenger RNA encoding a polypeptide with d-limonene synthase activity, to thereby induce a *Citrus* spp. plant defense response, reduce the d-limonene synthase activity, and reduce accumulation of endogenous d-limonene by at least 50 fold and cause an increase in non-d-limonene terpenoids as compared to a wildtype plant of the same *Citrus* spp.; and performing an assay to determine whether a *Citrus* spp. plant defense response is induced.

19. A method for reducing d-limonene in citrus fruit, comprising:

genetically transforming a plant of a *Citrus* spp., by introducing a transgene encoding a constitutively expressed RNA having at least one antisense RNA portion configured to trigger RNA silencing of at least an endogenous messenger RNA encoding a polypeptide with d-limonene synthase activity, to thereby reduce the d-limonene synthase activity, reduce accumulation of endogenous d-limonene by at least 50 fold and increase accumulation of non-d-limonene terpenoids as compared to a wildtype plant of the same *Citrus* spp.; and performing at least one assay to determine that the reduction in d-limonene synthase activity is sufficient to induce a *Citrus* spp. plant defense response in the plant.

20. The method according to claim 19, wherein the transgene has a sequence encoding an antisense sequence from a d-limonene synthase gene isolated from a *Citrus* spp.

* * * * *

SEQUENCE LISTING

<160> NUMBER OF SEQ ID NOS: 5

<210> SEQ ID NO 1

<211> LENGTH: 1824
<212> TYPE: DNA
<213> ORGANISM: Artificial Sequence
<220> FEATURE:
<223> OTHER INFORMATION: precursor nucleotide sequence for d-limonene
      synthase of Citrus spp.

<400> SEQUENCE: 1

```
atgtcttctt gcattaatcc ctcaaccttg gctacctctg taaatggttt caaatgtctt     60
cctcttgcaa caaatagagc agccatcaga atcatggcaa aaaataagcc agtccaatgc    120
cttgtcagca ccaaatatga taatttgaca gttgatagga gatcagcaaa ctaccaacct    180
tcaatttggg accatgattt tttgcagtca ctgaatagca actatacgga tgaaacatac    240
aaaagacgag cagaagagct gaagggaaaa gtgaagacag cgattaagga tgtaaccgag    300
cctctggatc agttggagct gattgataat ttgcaaagac ttggattggc ttatcatttt    360
gagcctgaga ttcggaacat attgcgtaat atccacaacc ataataaaga ttataattgg    420
agaaaagaaa atctgtatgc aacctcccctt gaattcagac tacttagaca acatggctat    480
cctgtttctc aagaggtttt cagtggtttt aaagacgaca aggtaggctt catttgtgat    540
gatttcaagg gaatactgag cttgcatgaa gcctcgtatt acagcttaga aggagaaagc    600
atcatggagg aggcctggca attcaccagt aagcatctta agaaatgat gatcatcagc    660
aacagcaagg aagaggatgt atttgtagca gaacaagcga agcgggcgct ggagctccct    720
ctgcattgga aagtgcctat gttagaggca aggtggttca tacacgttta tgagaaaaga    780
gaggacaaga accaccttttt acttgagctc gctaagttgg agtttaacac tttgcaggca    840
atttaccagg aagaacttaa agacatttca gggtggtgga aggatacagc tcttggagag    900
aaattgagct tgcgaggaa caggttggta gcgtccttct tatggagcat ggggatcgcg    960
tttgagcctc aattcgccta ctgcaggaga gtgctcacaa tctcgatagc cctaattaca   1020
gtgattgatg acatttatga tgtctatgga acattggatg aacttgagat attcactgat   1080
gctgttgaga ggtgggacat caattatggt ttgaagcacc ttccgggcta tatgaaaatg   1140
tgttttcttg ccctttacaa ctttgttaat gaatttgctt attacgttct caaacaacag   1200
gattttgata tgcttctgag cataaaacat gcatggcttg cttaataca agcctacttg   1260
gtggaggcga aatggtacca tagcaagtac acaccgaaac tggaagaata cttggaaaat   1320
ggattggtat caataacggg ccctttaatt ataacgattt catatctttc tggtacaaat   1380
ccaatcatta agaaggaact ggaatttcta gaaagtaatc cagatatagt tcactggtca   1440
tccaagattt tccgtctgca agatgatttg ggaacttcat cggacgagat acagagaggg   1500
gatgttccga aatcaatcca gtgttacatg catgaaactg gtgcctcgga ggaagttgct   1560
cgtgaacaca tcaaggatat gatgagacag atgtggaaga aggtgaatgc atacacagcc   1620
gataaagact ctcccttgac tcgaacaact gctgagttcc tcttgaatct tgtgcgaatg   1680
tcccatttta tgtatctaca tggagatggg catggtgttc aaaaccaaga gactatcgat   1740
gtcggctttta cattgctttt tcagcccatt cccttggagg acaaagacat ggctttcaca   1800
gcatctcctg gcaccaaagg ctga                                           1824
```

<210> SEQ ID NO 2
<211> LENGTH: 380
<212> TYPE: PRT
<213> ORGANISM: Artificial Sequence
<220> FEATURE:
<223> OTHER INFORMATION: polypeptide sequence of d-limonene synthase of
      SEQID:001

<400> SEQUENCE: 2

```
Met Ser Ser Cys Asn Ser Thr Ala Thr Ser Val Asn Gly Lys Cys Ala
1               5                   10                  15
Thr Asn Arg Ala Ala Arg Met Ala Lys Asn Lys Val Cys Val Ser Thr
            20                  25                  30
Lys Tyr Asp Asn Thr Val Asp Arg Arg Ser Ala Asn Tyr Ser Trp Asp
        35                  40                  45
His Asp Ser Asn Ser Asn Tyr Thr Asp Thr Tyr Lys Arg Arg Ala Lys
    50                  55                  60
Gly Lys Val Lys Thr Ala Lys Asp Val Thr Asp Asp Asn Arg Gly Ala
65                  70                  75                  80
Tyr His Arg Asn Arg Asn His Asn His Asn Lys Asp Tyr Asn Trp Arg
                85                  90                  95
Lys Asn Tyr Ala Thr Ser Arg Arg His Gly Tyr Val Ser Val Ser Gly
            100                 105                 110
Lys Asp Asp Lys Val Gly Cys Asp Asp Lys Gly Ser His Ala Ser Tyr
        115                 120                 125
Tyr Ser Gly Ser Met Ala Trp Thr Ser Lys His Lys Met Met Ser Asn
    130                 135                 140
Ser Lys Asp Val Val Ala Ala Lys Arg Ala His Trp Lys Val Met Ala
145                 150                 155                 160
Arg Trp His Val Tyr Lys Arg Asp Lys Asn His Ala Lys Asn Thr Ala
                165                 170                 175
Tyr Lys Asp Ser Gly Trp Trp Lys Asp Thr Ala Gly Lys Ser Ala Arg
            180                 185                 190
Asn Arg Val Ala Ser Trp Ser Met Gly Ala Ala Tyr Cys Arg Arg Val
        195                 200                 205
Thr Ser Ala Thr Val Asp Asp Tyr Asp Val Tyr Gly Thr Asp Thr Asp
    210                 215                 220
Ala Val Arg Trp Asp Asn Tyr Gly Lys His Gly Tyr Met Lys Met Cys
225                 230                 235                 240
Ala Tyr Asn Val Asn Ala Tyr Tyr Val Lys Asp Asp Met Ser Lys His
                245                 250                 255
Ala Trp Gly Ala Tyr Val Ala Lys Trp Tyr His Ser Lys Tyr Thr Lys
            260                 265                 270
Tyr Asn Gly Val Ser Thr Gly Thr Ser Tyr Ser Gly Thr Asn Lys Lys
        275                 280                 285
Ser Asn Asp Val His Trp Ser Ser Lys Arg Asp Asp Gly Thr Ser Ser
    290                 295                 300
Asp Arg Gly Asp Val Lys Ser Cys Tyr Met His Thr Gly Ala Ser Val
305                 310                 315                 320
Ala Arg His Lys Asp Met Met Arg Met Trp Lys Lys Val Asn Ala Tyr
                325                 330                 335
Thr Ala Asp Lys Asp Ser Thr Arg Thr Thr Ala Asn Val Arg Met Ser
            340                 345                 350
His Met Tyr His Gly Asp Gly His Gly Val Asn Thr Asp Val Gly Thr
        355                 360                 365
Asp Lys Asp Met Ala Thr Ala Ser Gly Thr Lys Gly
    370                 375                 380
```

<210> SEQ ID NO 3
<211> LENGTH: 26
<212> TYPE: DNA

```
<213> ORGANISM: Artificial Sequence
<220> FEATURE:
<223> OTHER INFORMATION: LAS-F

<400> SEQUENCE: 3
gagaggatcc atgtcttctt gcatta                                    26

<210> SEQ ID NO 4
<211> LENGTH: 25
<212> TYPE: DNA
<213> ORGANISM: Artificial Sequence
<220> FEATURE:
<223> OTHER INFORMATION: LS1-R

<400> SEQUENCE: 4
gagaggatcc tcagccttg gtgcc                                      25

<210> SEQ ID NO 5
<211> LENGTH: 25
<212> TYPE: DNA
<213> ORGANISM: Artificial Sequence
<220> FEATURE:
<223> OTHER INFORMATION: P35S-F

<400> SEQUENCE: 5
atctccactg acgtaaggga tgacg                                     25
```